(12) United States Patent
Zhang et al.

(10) Patent No.: US 10,632,071 B2
(45) Date of Patent: Apr. 28, 2020

(54) PREPARATION METHOD FOR CHARGE REVERSAL AND REVERSIBLY CROSSLINKED REDOX-SENSITIVE NANOMICELLES

(71) Applicant: Jiangnan University, Wuxi (CN)

(72) Inventors: Liping Zhang, Wuxi (CN); Ren Liu, Wuxi (CN); Caihua Ni, Wuxi (CN); Yuanyuan Ding, Wuxi (CN); Gang Shi, Wuxi (CN); Xinxin Sang, Wuxi (CN)

(73) Assignee: JIANGNAN UNIVERSITY, Wuxi, Jiangsu (CN)

( * ) Notice: Subject to any disclaimer, the term of this patent is extended or adjusted under 35 U.S.C. 154(b) by 0 days.

(21) Appl. No.: 15/751,577

(22) PCT Filed: Apr. 27, 2017

(86) PCT No.: PCT/CN2017/082114
§ 371 (c)(1),
(2) Date: Feb. 9, 2018

(87) PCT Pub. No.: WO2018/120544
PCT Pub. Date: Jul. 5, 2018

(65) Prior Publication Data
US 2019/0091147 A1    Mar. 28, 2019

(30) Foreign Application Priority Data
Dec. 26, 2016  (CN) .......................... 2016 1 1215858

(51) Int. Cl.
| | | |
|---|---|---|
| *A61K 9/107* | (2006.01) |
| *C08J 3/07* | (2006.01) |
| *C08J 3/12* | (2006.01) |
| *C08J 3/24* | (2006.01) |
| *A61K 47/34* | (2017.01) |
| *C08G 73/02* | (2006.01) |

(52) U.S. Cl.
CPC ............ *A61K 9/1075* (2013.01); *A61K 47/34* (2013.01); *C08G 73/028* (2013.01); *C08J 3/07* (2013.01); *C08J 3/24* (2013.01); *C08J 2379/02* (2013.01)

(58) Field of Classification Search
None
See application file for complete search history.

(56) References Cited

U.S. PATENT DOCUMENTS

2017/0168042 A1*  6/2017  Mattoussi ............. C07C 271/22

* cited by examiner

*Primary Examiner* — Michael J Feely
(74) *Attorney, Agent, or Firm* — IPro, PLLC

(57) ABSTRACT

Disclosed is a preparation method for charge reversal and reversibly crosslinked redox-sensitive nanomicelles, falling within the technical field of biomedical materials. The method comprises: synthesizing thiocinamide from lipoic acid and ethylenediamine under an N,N'-carbonyl diimidazole catalyst; and polymerizing thiocinamide, polyethylene glycol diglycidyl ether and lysine through a nucleophilic addition mechanism to prepare a poly(lysine-co-polyethylene glycol diglycidyl ether-co-thiocinamide) terpolymer. The micelle is endowed with excellent anti-protein nonspecific adsorption and enhanced cell uptake property through a self-assembly and protonation/deprotonation action; and a disulfide bond in lipoyl may form a linear polydisulfide structure under the action of 1,4-dithiothreitol, so that a micelle core is crosslinked, and a crosslinked structure is destroyed in the cell under a redox condition, and controlled release of a drug can be achieved. The Nanomicelle of the present invention is expected to be a carrier of drugs for treating cancers.

10 Claims, 6 Drawing Sheets

PREPARATION METHOD FOR CHARGE REVERSAL AND REVERSIBLY CROSSLINKED REDOX-SENSITIVE NANOMICELLES

TECHNICAL FIELD

The present invention relates to a preparation method for charge reversal and reversibly crosslinked redox-sensitive nanomicelles, falling within the technical field of biomedical materials.

BACKGROUND

After entering a human body, a drug nano-carrier is diluted by a great amount of body fluid, and thus becomes less stable. In order to increase stability, the carrier is subjected to hydrophilic shell crosslinking, hydrophobic core crosslinking or core-shell interface crosslinking, so as to reduce carrier dissociation caused by dilution. However, these traditional crosslinking manners also reduce the efficiency of drug release while stabilizing the carrier. Furthermore, a very small number of crosslinking structures are biocompatible and biodegradable. This greatly limits application of these carriers in the field of biological medicine.

Complex protein components in blood easily react with carriers carrying positive charges or active groups in the carriers to make the carriers gathered and removed out of the body. Carriers smoothly entering targeted parts reduce uptake of drug carriers by cells due to cell membrane rejection, thereby influencing the bioavailability of drugs. Recently, researchers apply a charge transfer caused by acid-sensitive bond breakage to drug carriers, such that the carriers are negatively charged during body circulation, thereby effectively avoiding interaction with proteins in blood; and when entering tumor tissues, the carriers are positively charged in a weak acid environment, so that interaction between the carriers and cancer cells can be enhanced, thereby improving uptake of carriers by cells. The charge transfer is advantageous in endowing the carriers with anti-protein adsorption performance and increasing cell uptake capability.

At present, there are few reports about reversible core-crosslinked drug carriers with reversible charges, reactions needed for providing charge reversal properties and cross-linking structures are complex, and most of formed materials cannot meet biodegradability, thereby reducing the application feasibility of such materials.

SUMMARY

To solve the foregoing technical problem, the objective of the present invention is to provide a preparation method for a reversibly crosslinked redox-sensitive Nanomicelle with reversible charges and excellent biocompatibility.

The present invention provides a preparation method for a reversibly crosslinked redox-sensitive Nanomicelle with reversible charges. The polymer s synthesized from three monomers namely polyethylene glycol diglycidyl ether, lysine and thiocinamide through a nucleophilic ring-opening reaction. A synthesis diagram is as shown in FIG. 1. To form a micelle in an appropriate hydrophilic-hydrophobic ratio, the molecular weight of the adopted polyethylene glycol diglycidyl ether is 315 g/mol. The feeding mole ratio of the three monomers is in a range of 1:0.9:0.1 to 1:0.1:0.9, and a component ratio can be adjusted to control the forming of the micelle and isoelectric points thereof. Three monomer units have respective functions in a Nanomicelle as follows. 1) Polyethylene glycol diglycidyl ether serves as a bridge connecting two small functional molecules and is excellent in biocompatibility. 2) Lysine is one of amino acids essential to a human body, carboxyl and amino in molecules of lysine can achieve protonation/deprotonation under different pH conditions so as to control charges on the surface of a carrier, and meanwhile, blood anti-protein adsorption and enhanced cell uptake property are achieved. 3) Lipoic acid is an antioxidant in the human body, a disulfide bond in a five-membered ring thereof can form a crosslinking structure with a plurality of adjacent disulfide bonds under the action of a catalytic amount of DTT, the crosslinking structure can be broken under the action of a high-concentration redox (such as GSH), and the special reversible crosslinking structure can stabilize body circulation of the carrier and can be destroyed under the action of high-concentration GSH inside a cell, thereby enhancing the targeted release capability of a drug.

In an embodiment of the present invention, the mole ratio of polyethylene glycol diglycidyl ether, lysine and thiocinamide is 1:0.7:0.3.

In an embodiment of the present invention, the mole ratio of polyethylene glycol diglycidyl ether, lysine and thiocinamide is 1:1:0.

In an embodiment of the present invention, the mole ratio of polyethylene glycol diglycidyl ether, lysine and thiocinamide is 1:0.5:0.5.

In an embodiment of the present invention, a mole ratio of polyethylene glycol diglycidyl ether, lysine and thiocinamide is 1:0.3:0.7.

The present invention also provides a preparation method for a reversibly crosslinked redox-sensitive Nanomicelle with reversible charges, sequentially comprising the following steps:

1) generating Lipoyl ethylene diamine (LAE) through a reaction between lipoic acid and ethylenediamine under the action of a catalyst N,N'-carbonyl diimidazole;

2) obtaining a coarse terpolymer solution from thiocinamide, polyethylene glycol diglycidyl ether with different molecular weights, and lysine through a nucleophilic addition reaction;

3) dialyzing and drying a coarse reaction solution to obtain pure polymer powder;

4) dissolving the powder, and dropwise adding ultra-pure water into the terpolymer solution slowly under continuous stirring;

5) after the step of dropwise adding the water is ended, stirring for a period of time, transferring the solution into a dialysis bag, and carrying out dialysis treatment to obtain a non-crosslinked Nanomicelle; and 6) under a nitrogen flow, adding a catalytic amount of DTT solution into a non-crosslinked micelle solution, carrying out stirring for 24 hours, and then carrying out dialysis for 24 hours, so as to obtain a crosslinked Nanomicelle solution.

Specifically, in the step 1), a catalyst adopted for an amidation reaction between lipoic acid and ethylenediamine is N,N'-carbonyl diimidazole, a reaction solvent is chloroform, and reaction products are extracted by using 10% sodium chloride and 1M sodium hydroxide respectively.

Specifically, in the step 2), polyethylene glycol diglycidyl ether of which the molecular weight is 315 g/mol is adopted for a nucleophilic reaction, and under this molecular weight, a polymer hydrophilic-hydrophobic ratio can be well controlled, so as to form a micelle.

Specifically, in the step 2), the mole ratio of three reaction components is in a range of 1:0.9:0.1 to 1:0.1:0.9, and an optimum reaction ratio can be selected according to an appropriate particle size and isoelectric point. The reaction solvent is a mixed solution of methyl alcohol and water, the volume ratio is 1:1, and the action is carried out for 3 days at the temperature of 50° C. under the nitrogen protection.

Specifically, in the step 3), a dialysis bag of which the molecular weight cutoff is 3500 is adopted for dialysis, and dialysis fluid is a mixed solution of methyl alcohol and water (v:v=1:1). The objective of the dialysis is to remove polymers with low molecular weight in favor of forming a micelle with a uniform particle size.

Specifically, in the step 4), a polymer is dissolved in dimethyl sulfoxide, and after the polymer is fully dissolved, ultra-pure water is dropwise added at the speed of 30 s/drop.

Specifically, in the step 5), after the step of dropwise adding the water is ended, stirring is carried out for two hours, the solution is transferred into the dialysis bag of which the molecular weight cutoff is 3500, and dialysis is carried out for not less than 24 hours, so as to obtain a pure non-crosslinked Nanomicelle solution.

Specifically, in the step 6), DTT is 10 mol % of lipoyl, and excessive DTT may result in that a disulfide bond is thoroughly broken and cannot be crosslinked. The reaction is carried out under a dark condition at the temperature of 25° C.

The present invention also provides application of a reversibly crosslinked redox-sensitive Nanomicelle with reversible charges in preparation of chemotherapeutic drug carriers. A micelle carries a hydrophobic anti-cancer drug through hydrophobic interaction, and meanwhile, a disulfide bond in a hydrophobic chain segment thiocinamide can be crosslinked under the action of a catalytic amount of DTT to form a more stable drug-carrying Nanomicelle. Due to a special physiological environment in a cancer cell, the content of GSH in a cytoplasm and a cell nucleus of the cancer cell can be up to 1000 times that in body blood, so that after a Nanomicelle which originally and stably entraps drug for circulation in the blood enters the cancer cell, the crosslinked disulfide bond is destroyed by high-concentration GSH redox, thereby achieving controlled release of a drug in the cell.

By means of the foregoing solutions, the present invention at least has the advantages as follows.

1. The preparation method of the present invention synthesizes a polymer by utilizing nucleophilic addition without addition of a catalyst, the reaction being mild and efficient.

2. During the nucleophilic addition process of lysine, the possibility of amino on a pendant group participating in the reaction under the influence of carboxyl is greatly reduced; and protonation/deprotonation of the remaining amino and carboxyl under different pH conditions can achieve excellent anti-protein adsorption property during body circulation.

3. The CMC value of the polymer Nanomicelle prepared in the present invention is in a range of 0.011 to 0.038 mg/mL, the Nanomicelle is negatively charged under the pH value of 7.4, and the charges on the surface of the micelle are transferred into positive charges under the pH value of 6.5, so that when the micelle reaches tumor tissues, the charges on the surface of the micelle are transferred into positive charges, uptake of drug carriers by cancer cells can be improved by means of an electrostatic action, and it is unnecessary to be bonded with a specific ligand, thereby not increasing the reaction difficulty.

4. A disulfide bond in the Nanomicelle can form a core crosslinked stable structure under the action of catalytic-amount DTT, so as to achieve stable circulation in a human body; and the structure is broken in quick response in a cell nucleus and cytoplasm containing high-concentration GSH. The Nanomicelle can be used for carrying an anti-cancer drug and achieving targeted release of the drug.

5. A polymer synthesized from raw materials namely polyethylene glycol diglycidyl ether and endogenous substances of a human body has excellent biocompatibility, the cell survival rates of cells L929 and Hela in Nanomicelle solutions with different concentrations being 90% or more.

The above is only the summary of the technical solutions of the present invention. In order to more clearly understand the technical means of the present invention and to implement in accordance with the content of the description, the detailed description will be made hereinafter in conjunction with preferred embodiments of the present invention and the drawings.

DETAILED DESCRIPTION

Figure 1:
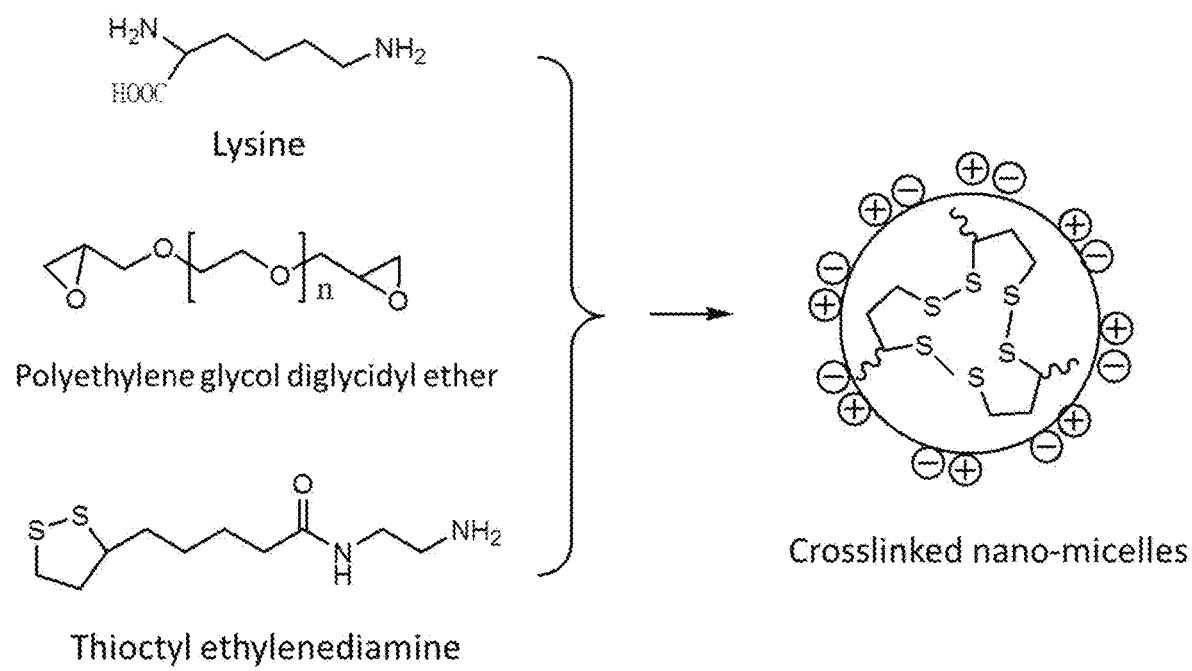
FIG. 1 is a schematic diagram of forming a crosslinked micelle in the present invention.

The detailed description of the invention will be made below in conjunction with the drawings and the embodiments. The following examples are used to illustrate the present invention, but not to limit the scope of the present invention.

EXAMPLE 1

1) Synthesis of Thiocinamide:

3.00 g of lipoic acid ($1.45 \times 10-2$ mol) and 2.59 g of N,N'-carbonyl diimidazole ($1.60 \times 10-2$ mol) are weighed, and dissolved in 30 mL of chloroform, and react for 1 hour at the temperature of 25° C. under the nitrogen protection, and then a mixed solution is transferred into a dropping funnel and dropwise added into a uniformly-stirred chloroform (30 mL) solution of ethylenediamine (8 mL, 0.12 mol), and reacts for 12 hours at the temperature of 25° C. under the nitrogen protection. After the reaction is ended, a reaction mixed solution is transferred into a separating funnel and extracted by using 10% NaCl (100 mL) and 1M NaOH (100 mL) respectively, organic phases are collected, and an organic solvent is removed by rotary evaporation to obtain a yellow gelatinous compound thiocinamide (2.2 g, 61%).

2) Synthesis of poly(lysine-co-polyethylene glycol diglycidyl ether-co-thiocinamide):

315 mg of polyethylene glycol diglycidyl ether (1 mmol), 102 mg of lysine (0.7 mmol) and 75 mg of thiocinamide (0.3 mmol) are weighed respectively and dissolved in 3 mL of a mixed solution of methyl alcohol and water (V:V=1:1), and react for 72 hours in a 25 mL single-opening flask at the temperature of 50° C. under the nitrogen protection. After the reaction is ended, a coarse solution is transferred into a dialysis bag of which the molecular weight cutoff is 3500, dialyzed for 3 days, and freeze-dried to obtain a yellow product. The corresponding dissolution ratio of polyethylene glycol diglycidyl ether, thiocinamide and lysine in a mixed solution is as shown in Table 1. The present invention provides only 4 terpolymer synthesis formulas. During a specific using process, the ratio of three monomers is adjusted according to application requirements of a Nanomicelle for different properties.

Figure 2:
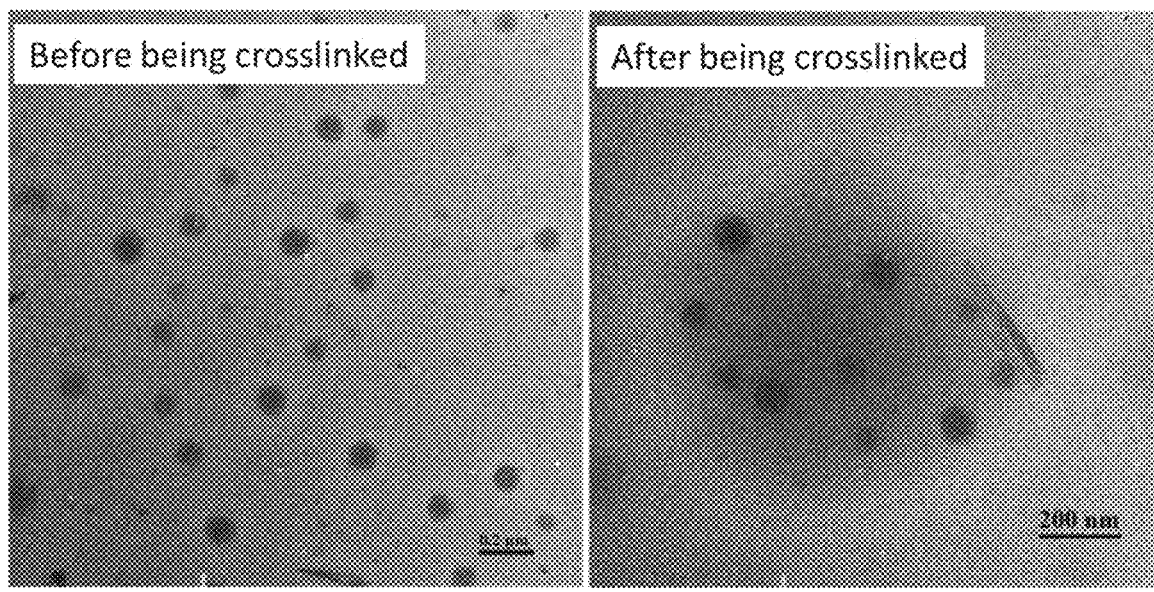
FIG. 2 is transmission electron microscope images of a reversibly crosslinked redox-sensitive Nanomicelle with reversible charges in the present invention before and after being crosslinked, where N4 is representative of a reversibly crosslinked redox-sensitive Nanomicelle with reversible charges obtained by a reaction among polyethylene glycol diglycidyl ether, thiocinamide and lipoic acid in a mole ratio of 1:0.3:0.7.

3) Preparation of Reversibly Crosslinked Redox-Sensitive Nanomicelle with Reversible Charges:

10 mg of a polymer is weighed and dissolved in 1 mL of dimethyl sulfoxide, and after the polymer is fully dissolved, 8 mL of ultra-pure water is dropwise added. After the step of dropwise adding the water is ended, stirring is carried out for 2 hours, the solution is transferred into the dialysis bag of which the molecular weight cutoff is 3500, and dialysis is carried out for 72 hours, so as to obtain a pure non-crosslinked Nanomicelle solution. The Nanomicelle is crosslinked under the atmosphere of feeding $N_2$, and a catalytic amount of DTT is added. Specifically, a DTT (77 μg, 0.5 μmol) solution is added into 10 mL of non-crosslinked $N_4$ micelle (1 mg/mL) solution, and stirred for 24 hours under a dark condition at the temperature of 25° C. Dialysis is carried out for 24 hours by means of a dialysis method to obtain a pure crosslinked Nanomicelle solution. FIG. 2 is transmission electron microscope images of a reversibly crosslinked redox-sensitive Nanomicelle with reversible charges before and after being crosslinked, where $N_4$ corresponds to a terpolymer obtained by a formula No. $N_4$ in Table 1, the micelle is a uniform and regular spherical micelle before and after being crosslinked, and the particle size of the crosslinked micelle is reduced by about 20 nm.

EXAMPLE 2

Figure 3:
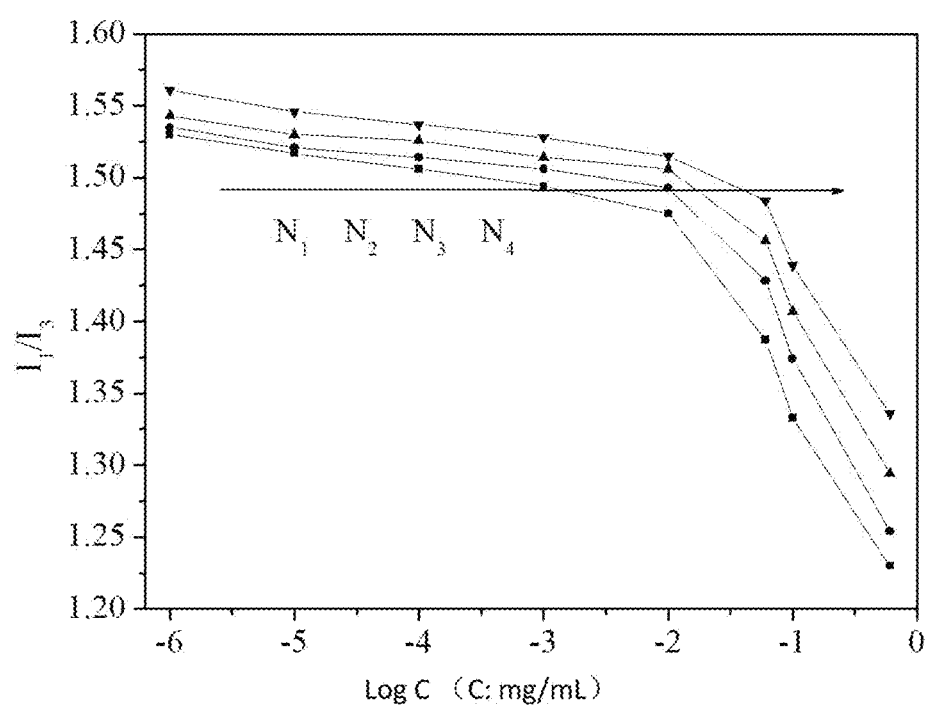
FIG. 3 is a critical micelle concentration of a reversibly crosslinked redox-sensitive Nanomicelle with reversible charges in the present invention, where N1, N2, N3 and N4 are representatives of a reversibly crosslinked redox-sensitive Nanomicelle with reversible charges obtained by a reaction among polyethylene glycol diglycidyl ether, thiocinamide and lipoic acid in a mole ratio of 1:1:0, 1:0.7:0.3, 1:0.5:0.5 and 1:0.3:0.7 respectively, and C is a polymer micelle concentration (mg/mL)

Measurement of Reversibly Crosslinked Redox-Sensitive Nanomicelle (CMC) with Reversible Charges:

The reversibly crosslinked redox-sensitive Nanomicelle solution with reversible charges obtained in the example 1 is diluted into a series of micelle solutions with different concentrations, and 4 mL of the micelle solution with each concentration is added into 30 μL of acetone solution of pyrene of which the concentration is $1.622 \times 10^{-5}$ g/mL, and incubated in a constant-temperature shaking incubator under the atmosphere of nitrogen for 24 hours at the temperature of 30° C. An emission spectrum is measured by utilizing a fluorescence spectrophotometer, a fluorescence excitation wavelength A is set as 333 nm, a scanning range λ is in a range of 350 nm to 500 nm, both an excitation slit width and an emission slit width are 5 nm, and the thickness of a sample pool is 1 cm. By measuring the fluorescence intensity of a series of Nanomicelle solutions with different concentrations at 373 nm ($l_1$) and 384 nm ($l_3$), a graph is drawn by taking a logarithm concentration as an X axis and $l_1/l_3$ as a Y axis, and the CMC value of a polymer Nanomicelle is calculated by using a curve discontinuity point. From FIG. 3, it can be seen that $N_1$, $N_2$, $N_3$ and $N_4$ have lower CMC values namely 0.011, 0.020, 0.030 and 0.038 mg/mL, which are increased along with the increase of the lysine content, and all have good anti-dilution stability.

TABLE 1

Table of terpolymer synthesis formula

| Nanomicelle number | Polyethylene glycol diglycidylether:thiocinamide:lysine (feeding mole ratio) | Polyethylene glycol diglycidyl ether/mg | Thiocinamide/mg | Lysine/mg |
|---|---|---|---|---|
| $N_1$ | 1:1:0 | 315 | 248 | 0 |
| $N_2$ | 1:0.7:0.3 | 315 | 174 | 44 |
| $N_3$ | 1:0.5:0.5 | 315 | 124 | 73 |
| $N_4$ | 1:0.3:0.7 | 315 | 75 | 102 |

Figure 4:
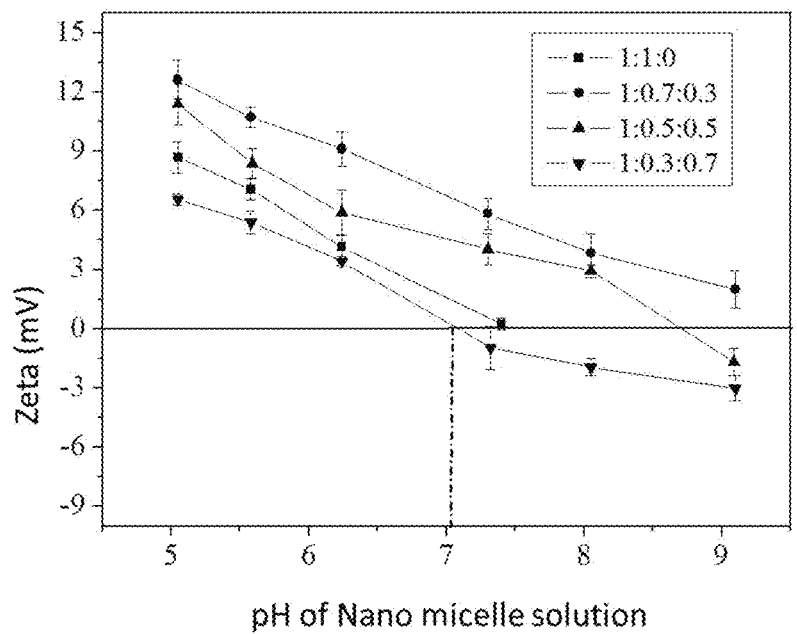
FIG. 4 is a zeta potential of a reversibly crosslinked redox-sensitive Nanomicelle with reversible charges in the present invention under different pH values, where N1, N2, N3 and N4 are representatives of a reversibly crosslinked redox-sensitive Nanomicelle with reversible charges obtained by a reaction among polyethylene glycol diglycidyl ether, thiocinamide and lipoic acid in a mole ratio of 1:1:0, 1:0.7:0.3, 1:0.5:0.5 and 1:0.3:0.7 respectively.

EXAMPLE 3 pH Sensitivity of Reversibly Crosslinked Redox-Sensitive Nanomicelle with Reversible Charges:

The reversibly crosslinked redox-sensitive Nanomicelle with reversible charges obtained in the example 1 is adjusted to different pH values by using 0.1 mol/L sodium hydroxide solution and a hydrochloric acid solution, and a Zeta potential is measured by utilizing a Zeta potentiometric analyzer. Consequently, from FIG. 4, it can be seen that when carrier material components are not added with lysine (namely $N_1$), the Nanomicelle is hardly charged under the condition of pH 7.4; and as the pH is decreased, positive charges on the surface of the Nanomicelle are increased. After the lysine component is added, carboxyl can be deprotonated under an alkaline condition, so that the Nanomicelle is negatively charged; the isoelectric point of a carrier can be adjusted by adjusting the ratio of three components; and when the mole ratio of polyethylene glycol diglycidyl ether, thiocinamide and lysine is 1:0.3:0.7 (namely $N_4$), the isoelectric point thereof is 7.04, the Nanomicelle can be negatively charged under the condition of pH 7.4, and charges on the surface of the micelle are transferred into positive charges under the condition of pH 6.5.

When the mole ratio of polyethylene glycol diglycidyl ether, thiocinamide and lysine is 1:0.3:0.7, the particle size of the Nanomicelle is relatively appropriate, and when pH is equal to 7.04, charge transfer is achieved. The micelle can be endowed with anti-protein adsorption and enhanced cell uptake property. Therefore, Nanomicelles mentioned in the following examples of the present invention refer to the Nanomicelle under this ratio unless otherwise specified.

EXAMPLE 4

Figure 5:
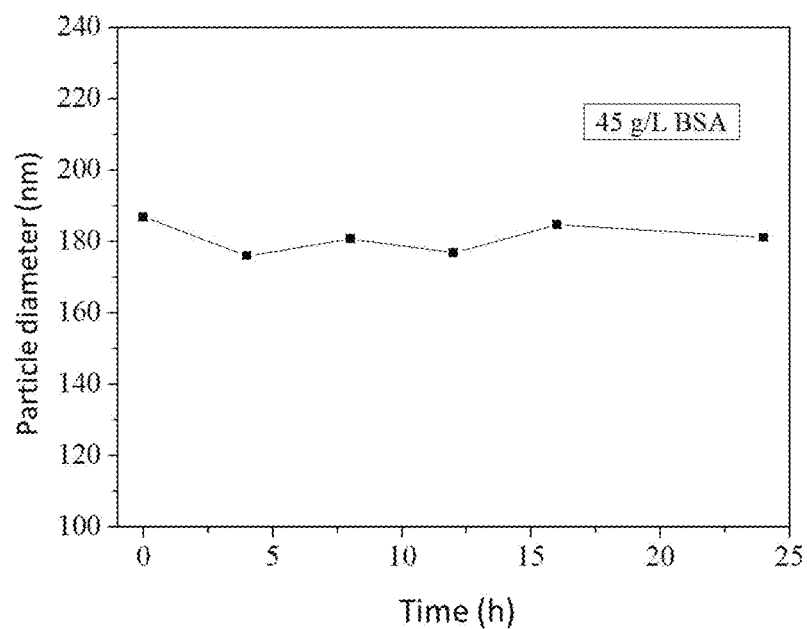
FIG. 5 is a particle size change of a reversibly crosslinked redox-sensitive Nanomicelle with reversible charges in the present invention after being incubated in a protein solution for 24 hours, where in a reversibly crosslinked redox-sensitive Nanomicelle with reversible charges obtained by a reaction among polyethylene glycol diglycidyl ether, thiocinamide and lipoic acid in a mole ratio of 1:0.3:0.7, BSA serves as a model protein of which the concentration is 45 g/L.

Anti-Protein Nonspecific Adsorption Property of Reversibly Crosslinked Redox-Sensitive Nanomicelle with Reversible Charges:

The reversibly crosslinked redox-sensitive Nanomicelle ($N_4$) with reversible charges obtained in the example 1 is put into a bovine serum albumin solution of which the concentration is 45 g/L, a particle size change of the Nanomicelle is tested by using a laser light scattering instrument within different periods, and the protein adsorption influence is observed. Consequently, as shown in FIG. 5, BSA in the figure is bovine serum albumin, the particle size of the Nanomicelle $N_4$ is not greatly changed within an observation period of 24 hours, and it is shown that a negatively-charged Nanomicelle can effectively reject protein adsorption and can be stably circulated in a human body.

EXAMPLE 5

Figure 6:
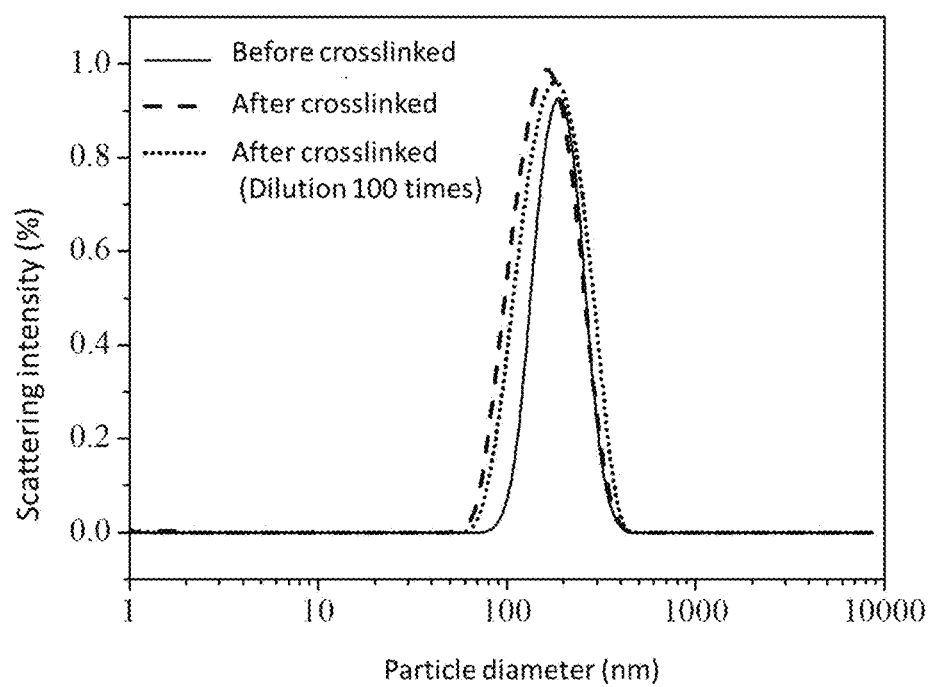
FIG. 6 is a particle size change of a reversibly crosslinked redox-sensitive Nanomicelle with reversible charges in the present invention, where N4 is representative of a reversibly crosslinked redox-sensitive Nanomicelle with reversible charges obtained by a reaction among polyethylene glycol diglycidyl ether, thiocinamide and lipoic acid in a mole ratio of 1:0.3:0.7.

Anti-Dilution Stability of a Reversibly Crosslinked Redox-Sensitive Nanomicelle with Reversible Charges:

The reversibly crosslinked redox-sensitive Nanomicelle ($N_4$, 0.5 mg/mL) with reversible charges obtained in the example 1 is diluted by 100 times by using ultra-pure water to make its concentration lower than the CMC value, and the particle size change of the Nanomicelle is tested by using a laser light scattering instrument. Consequently, as shown in FIG. 6, the particle size of the crosslinked Nanomicelle is reduced from 187 nm to 162 nm, which is consistent with a result obtained by a transmission electron microscope image. The crosslinked Nanomicelle is diluted to be the CMC value or below, it is discovered that the particle size and the distribution thereof are not greatly changed, and it is shown that the crosslinked Nanomicelle has strong anti-dilution stability and can be prevented from dissociation in case of dilution of a great amount of body fluid.

EXAMPLE 6

Figure 7:
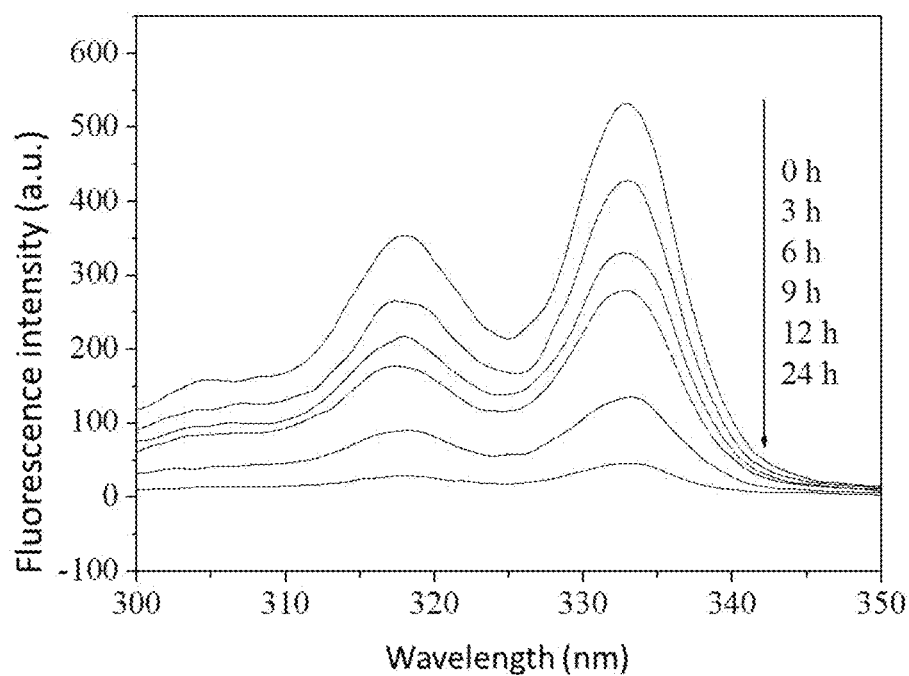
FIG. 7 is a fluorescence intensity change of a reversibly crosslinked redox-sensitive Nanomicelle with reversible charges in the present invention in a 10 mmol/L glutathione solution, where a reversibly crosslinked redox-sensitive Nanomicelle with reversible charges is obtained by a reaction among polyethylene glycol diglycidyl ether, thiocinamide and lipoic acid in a mole ratio of 1:0.3:0.7.

Redox Sensitivity of Reversibly Crosslinked Redox-Sensitive Nanomicelle with Reversible Charges:

The reversibly crosslinked redox-sensitive Nanomicelle ($N_4$, 4 mL, 1 mg/mL) with reversible charges obtained in the example 1 is added into an acetone solution of pyrene, so that the concentration of the pyre is $5.0 \times 10^{-6}$ mol/L.; the Nanomicelle is incubated in a constant-temperature shaking incubator for 24 hours at the temperature of 30° C., and a GSH solution is added to make the GSH concentration reach 10 mol/L; and then within a specific time interval, an emission spectrum of the pyrene in the micelle solution is measured by utilizing a fluorescence spectrophotometer, an emission wavelength is 395 nm, and both an excitation slit width and an emission slit width are 5 nm. Consequently, as shown in FIG. 7, as time increases, the fluorescence intensity of the pyrene is gradually reduced, and it is shown that the pyrene enters a hydrophilic environment from a hydrophobic environment. The reason for this phenomenon is that a disulfide bond of a micelle core is broken under the action of GSH to destroy an original micelle structure so as to release the pyrene wrapped by the micelle.

EXAMPLE 7

Figure 8:
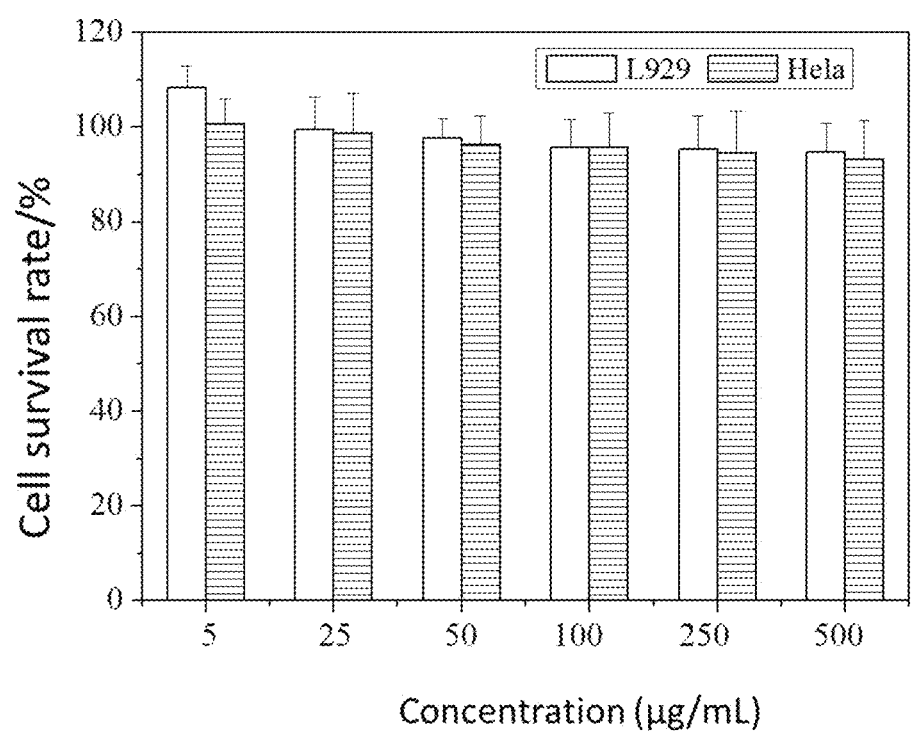
FIG. 8 is a cytotoxicity result of a reversibly crosslinked redox-sensitive Nanomicelle with reversible charges in the present invention.

Biocompatibility of Reversibly Crosslinked Redox-Sensitive Nanomicelle with Reversible Charges:

A reversibly crosslinked redox-sensitive Nanomicelle $N_4$ with reversible charges obtained in the example 1 is taken as a research object. The cytotoxicity of a Nanomicelle is tested by using an MTT method. A cervical cancer cell (Hela cell) or mouse fibroblast (L929 cell) growing in a logarithmic phase is digested by trypsin (0.25%), blown and scattered by using a DMEM culture medium containing 10% fetal calf serum, diluted into a cell suspension of which the concentration is $1.0 \times 10^4$ cells/mL by using the culture medium, inoculated to a 96-pore plate in 100 μL per pore, cultured in a constant-temperature incubator for 24 h, and then added into 100 μL of DMEM complete medium containing different polymer concentrations (5, 25, 50, 100, 250 and 500 μg/mL) respectively after leaving from the culture medium. Each group is provided with six complex pores, culture is carried out for 24 hours, and then the culture medium is removed. Each pore is added with 20 μL of MTT solution (5 mg/mL), culture is continuously carried out for 4 hours, and then the solution in the pore plate is removed. Each pore is added with 150 μL of dimethyl sulfoxide, formazan generated from living cells is dissolved by shaking, absorbancy is measured by using an ELIASA at 570 nm, and the cell survival rate is calculated. Consequently, as shown in FIG. 8, the cell survival rates of cells L929 and Hela in Nanomicelle solutions with different concentrations are 90% or more, and it is shown that the Nanomicelle has excellent biocompatibility.

What is claimed is:

1. A method for preparing charge reversal and reversibly crosslinked redox-sensitive nanomicelles, comprising the following sequential steps:
   1) generating Lipoyl ethylene diamine (LAE) by reacting lipoic acid and ethylenediamine in the presence of a catalyst;

2) obtaining a coarse terpolymer solution by polymerizing the LAE, polyethylene glycol diglycidyl ether and lysine in a solvent, through a nucleophilic addition reaction;

3) dialyzing and drying the coarse terpolymer solution to obtain a powder of pure terpolymer;

4) dissolving the pure terpolymer powder in a solvent to form a terpolymer solution, and slowly adding ultra-pure water dropwise into the terpolymer solution, while continuously stirring;

5) stirring the terpolymer solution for a period of time after the addition of ultra-pure water is completed, transferring the terpolymer solution into a dialysis bag, and dialyzing the terpolymer solution to obtain a pure non-crosslinked nano-micelle solution; and 6) under a nitrogen flow, adding a catalytic amount of 1,4-dithiothreitol solution (DTT) to the pure non-crosslinked nano-micelle solution and stirring for 24 hours to obtain a crosslinked nano-micelle solution, and dialyzing the crosslinked nano-micelle solution for 24 hours to obtain a pure crosslinked nano-micelle solution.

2. The method according to claim 1, wherein step 1) comprises: dissolving lipoic acid and a N,N'-carbonyl diimidazole catalyst in chloroform; allowing the resulting solution to partially react yielding a mixed solution of reacted and unreacted lipoic acid; reacting the mixed solution with a solution of ethylenediamine dissolved in chloroform, to form a reaction mixed solution containing LAE; and exacting the reaction products of the reaction mixed solution using 10% sodium chloride and 1M sodium hydroxide.

3. The method according to claim 1, wherein in step 2), the mole ratio of the LAE, the polyethylene glycol diglycidyl ether, and the lysine is in a range of 1:0.9:0.1 to 1:0.1:0.9.

4. The method according to claim 1, wherein in step 2), the solvent is a mixed solution of methyl alcohol and water having a volume ratio of 1:1; and the polymerization reaction is carried out for 3 days at a temperature of 50° C.

5. The method according to claim 1, wherein in step 3), dialyzing is performed with a dialysis bag having a molecular weight cutoff 3500 and a dialysis fluid, wherein the dialysis fluid is a mixed solution of methyl alcohol and water having a volume ratio of 1:1.

6. The method according to claim 1, wherein in step 4), the solvent is dimethyl sulfoxide, and the ultra-pure water is added at a speed of 30 s/drop.

7. The method according to claim 1, wherein in step 5), the stirring is carried out for two hours; the dialysis bag has a molecular weight cutoff of 3500; and dialyzing is carried out for not less than 24 hours.

8. The method according to claim 1, wherein in step 6), 1,4-dithiothreitol is added in an amount of 10 mol % of lipoyl groups; and crosslinking is carried out under a dark condition at a temperature of 25° C.

9. A redox-sensitive reversible crosslinked nano-micelle with reversible charges, prepared by using the method of claim 1.

10. A pharmaceutical composition comprising the redox-sensitive reversible crosslinked nano-micelle with reversible charges of claim 9.

* * * * *